(12) United States Patent
Sarks et al.

(10) Patent No.: US 10,920,247 B2
(45) Date of Patent: Feb. 16, 2021

(54) METHODS AND SYSTEMS FOR PROPAGATION OF A MICROORGANISM USING A PULP MILL AND/OR A PAPER MILL WASTE BY-PRODUCT, AND RELATED METHODS AND SYSTEMS

(71) Applicant: POET Research, Inc., Sioux Falls, SD (US)

(72) Inventors: Cory J. Sarks, Sioux Falls, SD (US); Alex C. Johnson, Westbrook, MN (US); Malgorzata M. Slupska, Sioux Falls, SD (US); Zachary J. Karl, Sioux Falls, SD (US); Melanie A. Eichmann, Canistota, SD (US)

(73) Assignee: POET Research, Inc., Sioux Falls, SD (US)

( * ) Notice: Subject to any disclaimer, the term of this patent is extended or adjusted under 35 U.S.C. 154(b) by 52 days.

(21) Appl. No.: 16/122,401

(22) Filed: Sep. 5, 2018

(65) Prior Publication Data
US 2019/0071696 A1 Mar. 7, 2019

Related U.S. Application Data (60) Provisional application No. 62/554,434, filed on Sep. 5, 2017, provisional application No. 62/554,430, filed on Sep. 5, 2017.

(51) Int. Cl.
| | | |
|---|---|---|
| *C12P 7/10* | (2006.01) |
| *C12N 1/24* | (2006.01) |
| *C12R 1/865* | (2006.01) |
| *C12P 7/12* | (2006.01) |
| *C12P 7/08* | (2006.01) |
| *C12N 1/18* | (2006.01) |

(52) U.S. Cl.
CPC ............... *C12P 7/10* (2013.01); *C12N 1/18* (2013.01); *C12N 1/24* (2013.01); *C12P 7/08* (2013.01); *C12P 7/12* (2013.01); *C12R 1/865* (2013.01)

(58) Field of Classification Search
CPC ..... C12N 1/18; C12N 1/24; C12P 7/08; C12P 7/10; C12P 7/12; C12R 1/865
See application file for complete search history.

(56) References Cited

U.S. PATENT DOCUMENTS

| | | | |
|---|---|---|---|
| 5,508,183 A | 4/1996 | Scott et al. |
| 5,637,502 A | 6/1997 | Scott et al. |
| 7,354,743 B2 | 4/2008 | Vlasenko et al. |
| 7,708,214 B2 | 5/2010 | Medoff |
| 7,842,490 B2 | 11/2010 | Felby et al. |
| 7,943,350 B2 | 5/2011 | Vlasenko et al. |
| 7,972,826 B2 | 7/2011 | Larsen et al. |
| 7,980,495 B2 | 7/2011 | Medoff |
| 8,058,041 B2 | 11/2011 | Berlin et al. |
| 8,110,383 B2 | 2/2012 | Jönsson et al. |
| 8,236,535 B2 | 8/2012 | Medoff et al. |
| 8,367,378 B2 | 2/2013 | Balan et al. |
| 8,413,915 B2 | 4/2013 | Medoff |
| 8,426,160 B2 | 4/2013 | Soong et al. |
| 8,450,094 B1 | 5/2013 | Narendranath et al. |
| 8,460,900 B2 | 6/2013 | Zhou |
| 8,544,773 B2 | 10/2013 | Medoff |
| 8,815,561 B2 | 8/2014 | Liu et al. |
| 8,852,901 B2 | 10/2014 | Medoff et al. |
| 8,900,457 B2 | 12/2014 | Lee et al. |
| 9,034,631 B2 | 5/2015 | Narendranath et al. |
| 9,133,278 B2 | 9/2015 | Slupska et al. |
| 9,193,982 B2 | 11/2015 | Sjoede et al. |
| 9,234,167 B2 | 1/2016 | Narendranath et al. |
| 9,340,767 B2 | 5/2016 | Narendranath |
| 9,359,620 B2 | 6/2016 | Medoff et al. |
| 9,359,621 B2 | 6/2016 | Soong et al. |
| 9,399,782 B2 | 7/2016 | Smith et al. |
| 9,416,376 B2 | 8/2016 | Narendranath et al. |
| 9,428,722 B2 | 8/2016 | Medoff et al. |
| 9,540,664 B2 | 1/2017 | Lewis et al. |
| 9,663,807 B2 | 5/2017 | Narendranath et al. |
| 9,850,512 B2 | 12/2017 | Min et al. |
| 9,896,358 B2 | 2/2018 | Pereira et al. |
| 9,914,948 B2 | 3/2018 | Del Rio et al. |
| 10,435,719 B2 * | 10/2019 | Smits ...................... C12R 1/645 |
| 2009/0035826 A1 | 2/2009 | Tolan et al. |
| 2011/0250638 A1 | 10/2011 | Sjoede et al. |
| 2014/0004573 A1 | 1/2014 | Medoff et al. |
| 2015/0018584 A1 | 1/2015 | Parekh et al. |
| 2015/0275432 A1 | 10/2015 | Retsina |

(Continued)

FOREIGN PATENT DOCUMENTS

| | | |
|---|---|---|
| WO | 2007070756 A2 | 6/2007 |
| WO | 2008128253 A1 | 10/2008 |

(Continued)

OTHER PUBLICATIONS

"Green Liquor", Safety Data Sheet, NA GHS SDS, May 24, 2018, (9 pages).

(Continued)

*Primary Examiner* — Ruth A Davis
(74) *Attorney, Agent, or Firm* — Kagan Binder, PLLC (57) ABSTRACT

The present disclosure relates to using a source of one or more monosaccharides derived from a pulp or paper mill waste by-product for propagating microorganisms (e.g., yeast or bacteria). If desired, after propagation, the microorganisms can then be used to ferment one or more monosaccharides derived from a pulp or paper mill waste by-product into one or more biochemicals. Optionally, a stillage composition can be included in propagation medium to facilitate propagation and/or a stillage composition can be used to facilitate enzymatic hydrolysis of oligosaccharides and/or polysaccharides in a pulp or paper mill waste by-product to form monosaccharides.

20 Claims, 3 Drawing Sheets

(56) References Cited

U.S. PATENT DOCUMENTS

| | | |
|---|---|---|
| 2015/0368679 A1 | 12/2015 | Narendranath et al. |
| 2016/0289707 A1 | 10/2016 | Grassi et al. |
| 2017/0081687 A1 | 3/2017 | Zayrel et al. |
| 2017/0204440 A1 | 7/2017 | Retsina et al. |
| 2017/0240940 A1 | 8/2017 | Medoff et al. |
| 2018/0155750 A1 | 6/2018 | Balaban et al. |
| 2018/0171285 A1 | 6/2018 | Narendranath et al. |
| 2019/0002940 A1 | 1/2019 | Karl |
| 2019/0256873 A1 | 8/2019 | Sarks et al. |

FOREIGN PATENT DOCUMENTS

| | | |
|---|---|---|
| WO | 2008137639 A1 | 11/2008 |
| WO | 2009045527 A1 | 4/2009 |
| WO | 2012103281 A2 | 8/2012 |
| WO | 2014160402 A1 | 10/2014 |
| WO | 2017091361 A1 | 6/2017 |
| WO | 2017201233 A1 | 11/2017 |
| WO | 2017218380 A1 | 12/2017 |

OTHER PUBLICATIONS

Product information for "Magnesium Lignosulfonate Solution, Intermediate, and Heavy", Cosmo Specialty Fibers Inc., Jun. 1, 2018, (3 pages).

"Black Liquor", Safety Data Sheet, Retrieved from https://www.westrock.com/en/customer-resources#safety-data-sheets--sds-, on Aug. 23, 2018, (10 pages).

Unpublished Utility U.S. Appl. No. 16/220,993, filed Dec. 14, 2018.

Unpublished Utility U.S. Appl. No. 16/193,485, filed Nov. 16, 2018.

International Search Report for International Application No. PCT/US2018/049562, dated Nov. 29, 2018 (6 pages).

Pinel et al., "*Saccharomyces cerevisiae* Genome Shuffling through Recursive Population Mating Leads to Improved Tolerance to Spent Sulfite Liquor", Applied and Environmental Microbiology, vol. 77, No. 14, pp. 4736-4743, Jul. 15, 2011, (9 pages).

Johansson et al., "Fermentation performance and physiology of two strains of *Saccharomyces cerevisiae* during growth in high gravity spruce hydrolysate and spent sulphite liquor", BMV Biotechnology, BIOMED Central LTD., vol. 14, No. 1, p. 47, May 21, 2014, (9 pages).

\* cited by examiner

METHODS AND SYSTEMS FOR PROPAGATION OF A MICROORGANISM USING A PULP MILL AND/OR A PAPER MILL WASTE BY-PRODUCT, AND RELATED METHODS AND SYSTEMS

CROSS REFERENCE TO RELATED APPLICATIONS

This application claims the benefit of U.S. Provisional Patent Application Ser. No. 62/554,430, filed Sep. 5, 2017, and U.S. Provisional Patent Application Ser. No. 62/554,434, filed Sep. 5, 2017, wherein the entire disclosure of said applications is incorporated herein by reference.

BACKGROUND

The present disclosure relates to propagating microorganisms that can be used in fermentation. Propagating microorganisms involves reproducing the microorganisms to increase the quantity of said microorganisms.

SUMMARY

The present disclosure includes embodiments of a method of propagating a microorganism, the method comprising:
  a) providing a propagation medium comprising a source of one or more monosaccharides derived from a pulp or paper mill waste by-product;
  b) providing a first cell mass of a microorganism that can convert at least a portion of the one or more monosaccharides into a biochemical;
  d) combining the propagation medium and the first cell mass of the microorganism to form a propagation composition, wherein the propagation composition is exposed to conditions to propagate the first cell mass of the microorganism into a second cell mass of the microorganism.

The present disclosure also includes embodiments of a system for propagating a microorganism, the system comprising:
  a) a source of one or more monosaccharides derived from a pulp or paper mill waste by-product;
  b) a source of a first cell mass of a microorganism that can covert the one or more monosaccharides into a biochemical;
  d) at least one vessel in fluid communication with the source of the one or more monosaccharides and the source of the first cell mass of the microorganism, wherein the at least one vessel is configured to combine at least a portion of the source of the one or more monosaccharides and the source of the first cell mass of the microorganism to form a propagation composition, wherein the vessel is also configured to expose the propagation composition to conditions to propagate the first cell mass of the microorganism into a second cell mass of the microorganism.

The present disclosure also includes embodiments of a method of processing a pulp or paper mill waste by-product, wherein the method comprises:
  a) forming a liquefaction composition, wherein the liquefaction composition comprises:
    i) a pulp or paper mill waste by-product;
    ii) an ionic stabilizing component; and
    iii) one or more enzymes that can hydrolyze at least a portion of one or more polysaccharides in the pulp mill or a paper mill waste by-product;
  b) exposing the liquefaction composition to conditions to hydrolyze at least a portion of one or more polysaccharides in the pulp mill or a paper mill waste by-product and form a liquefied composition.

The present disclosure also includes embodiments of a system for processing pulp mill or a paper mill waste by-product, wherein the system comprises:
  a) at least one liquefaction tank reactor containing a liquefaction composition, wherein the liquefaction composition comprises:
    i) a pulp or paper mill waste by-product;
    ii) an ionic stabilizing component; and
    iii) one or more enzymes that can hydrolyze at least a portion of one or more polysaccharides in the pulp mill or a paper mill waste by-product, wherein the at least one liquefaction tank reactor is configured (adapted) to expose the liquefaction composition to conditions to hydrolyze at least a portion of one or more polysaccharides in the pulp mill or a paper mill waste by-product and form a liquefied composition.

DETAILED DESCRIPTION

Disclosed in embodiments herein are methods and systems for propagating microorganisms into a larger population of microorganisms. Propagating a microorganism can also be referred to as "seed fermentation." After propagation ("seed fermentation"), the larger population of microorganisms can be used to convert one or more monosaccharides into one or more biochemicals (e.g., via fermentation), especially on an industrial scale.

In addition to increasing the cell count of a microorganism, it is believed that methods and systems according to the present disclosure can help create a more robust microorganism during propagation by using a propagation medium that includes a source of monosaccharides during propagation that is the same or similar to the source of monosaccharides used during fermentation (e.g., a sludge and/or liquor derived from a pulp or paper mill waste by-product). This can also be referred to as "conditioning" the microorganism.

Microorganisms that can convert one or more monosaccharides into a biochemical include, e.g., bacteria and/or fungi such as yeast. A wide variety of biochemicals can be produced by microorganisms. In some embodiments, a biochemical includes one or more biofuels such as ethanol, butanol, and the like. In some embodiments, the microorganism includes one or more ethanologenic microorganisms referred to as "ethanologens". As used herein, an "ethanologen" refers to a microorganism that can convert one or more monosaccharides (e.g., glucose, xylose, and the like) into at least ethanol.

Exemplary yeast and other fungi include the genus of, *Aspergillus, Candida, Pichia*, (*Hansenula*), *Phanerochaete, Kloeckera* (*Hanseniaspora*), *Kluyveromyces, Rhodotorula, Torulopsis, Zygosaccharomyces, Yarrowia*, and *Saccharomyces*. In some embodiments, the yeast is a strain of *Saccharomyces cerevisiae* yeast. In some embodiments, the microorganism to be propagated includes genetically modified yeast such as genetically modified *Saccharomyces cerevisiae* that can convert glucose and xylose into a biochemical such as ethanol.

A wide variety of microorganism population sizes (e.g., first cell mass) can be combined with a propagation medium to form a propagation composition for propagation (reproduction). In some embodiments, a first cell mass of the microorganism is $5 \times 10^{\wedge}6$ cells per milliliter of propagation composition or less, $1 \times 10^{\wedge}6$ cells per milliliter of propagation composition or less, $5 \times 10^{\wedge}5$ cells per milliliter of propagation composition or less, or even $1 \times 10^{\wedge}5$ cells per milliliter of propagation composition or less.

Propagating a microorganism according to the present disclosure includes combining a first cell mass of a microorganism with at least a source of one or more monosaccharides derived from a pulp or paper mill waste by-product under conditions to reproduce the number of microorganisms and form a second cell mass that is greater in cell number as compared to the first cell mass.

A source of one or more monosaccharides derived from a pulp or paper mill waste by-product (waste stream) can function as a carbon source and/or as a nutrient source for the microorganisms. As used herein, a "carbon source" refers to one or more compounds that include at least one carbon atom and can be used by a microorganism primarily as an energy source to grow and/or reproduce to create additional microorganisms. Exemplary carbon sources include monosaccharides such as glucose, fructose, galactose, mannose, xylose and the like; disaccharides such as lactose, maltose, sucrose, cellobiose and the like; oligosaccharides; polysaccharides such as cellulose, hemicelluloses, starch, xylan and the like; single carbon substrates including only one carbon atom such as methanol; and polyols such as glycerol, but not limited thereto. As used herein, a "nutrient source" refers to one or more materials that can be used by a microorganism primarily as an enzyme cofactor and/or as building blocks of molecules to grow and/or reproduce to create additional microorganisms. A nutrient source can be different from a carbon source or can be used as a carbon source as well.

Non-limiting examples of a waste by-products (streams) from a pulp or paper mill that can be used as a source of one or more monosaccharides according to the present disclosure include sludge, liquor, combinations of these, and the like.

As used herein, a "sludge" refers to one or more waste by-products (also referred to as a "reject") from a pulp or a paper mill that includes dissolved and/or suspended solids. Such sludges include relatively short fibers of cellulosic material that include one or more polysaccharides such as hemicellulose and cellulose. In some embodiments, a sludge can include a pulp sludge and/or a paper sludge, which are by-products from pulp and paper mills, respectively.

Pulp and/or paper sludges can include one or more additives. For example, paper sludge can include one or more paper-making additives such as clays, dyes, inks, and the like.

As used herein, a "liquor" refers to one or more waste by-products (streams) from a pulp and/or a paper mill and can include water and primarily dissolved solids including one or more monosaccharides. Exemplary monosaccharides include glucose, xylose, mannose, galactose, and mixtures thereof. In some embodiments, a liquor may include relatively minor amounts of one or more oligosaccharides and/or one or more polysaccharides.

For illustration purposes, two nonlimiting examples of pulping processes that can generate one or more "liquor" waste by-products as a source of one or more monosaccharides for use according to the present disclosure include chemical pulping processes known as the kraft(alkaline) process and the sulphite (acidic) process. Each of these processes use aqueous chemicals to degrade wood chips and recover pulp. The aqueous chemicals form a liquor (spent liquor) that include water soluble substances such as lignin, polysaccharides such as hemicellulose (and oligosaccharides and monosaccharides thereof). The spent liquor (a waste by-product liquor) can be separated from the pulp and used in a propagation medium and/or be fermented as described herein below.

In the kraft process, the pulping chemicals include sodium hydroxide and sodium sulphide in a solution known as white liquor. The combination of the spent liquor after digesting wood chips in the kraft process and pulp wash water is known as weak black liquor. The weak black liquor can be concentrated via an evaporator system to form heavy black liquor with a total solids content of approximately 55-70 percent. Heavylack liquor can include one or more of lignin, hemicellulose, cellulose, sodium carbonate, sodium sulfate, sodium sulfide, sodium hydroxide, hydrogen sulfide, methyl mercaptan, dimethyl sulfide, dimethyl disulfide, and other inorganic salts. In some embodiments, a heavy black liquor can include 30-60 percent hemicellulose and cellulose based on the total weight of the heavy black liquor, and 20-50 percent lignin based on the total weight of the heavy black liquor. In some embodiments, heavy black liquor can have a pH in the range from 11-13.

Heavy black liquor can be further processed at a pulp mill in a recovery boiler to generate useful steam (e.g., for a paper mill) and to allow for the recovery and recycle of the cooking chemicals as green liquor. Water is typically added so that green liquor has a water content of from about 70-90 percent by total weight of the green liquor. Green liquor can have a pH in the range from 13-14. The resultant green liquor can then be converted to white liquor for return to the wood digesters.

Black liquor, green liquor, and white liquor are also described in U.S. Pat. No. 8,894,818 (Schinski et al.), wherein the entirety of said patent document is incorporated herein by reference.

In the sulphite process, the pulping chemicals can include a mixture of metal (sodium, magnesium, potassium, or calcium) sulphite and ammonium sulphite. The spent liquor after digesting wood chips in the sulphite process is known as red or brown liquor.

Other nonlimiting examples of a liquor include a pre-hydrolysate liquor and a COEL liquor. A pre-hydrolysate liquor is derived from a wood chip digestion process that uses steam and/or hot water. A "COEL" liquor refers to a concentrated oxygen extraction liquor.

A pulp or paper mill waste by-product can be transported to a biorefinery for processing according to the present disclosure. In some embodiments, pulping and/or papermaking facilities can be co-located together with biorefineries to facilitate transferring sludge to the biorefinery for processing according to the present disclosure.

A pulp or paper mill waste by-product can be provided to a biorefinery with a range of total solids content (dissolved and undissolved solids). In some embodiments, a pulp or paper mill waste by-product (sludge or liquor) can include water and have a total solids content from 0.5-90%, from 2-80%, or even from 20-60% (e.g., about 40%).

The solids content of a pulp or paper mill waste by-product can be adjusted as desired before hydrolysis and/or propagation. If the solids content of a pulp or paper mill waste by-product is too high it can be diluted to a target solids content using a variety of liquids such as used process water from the biorefinery and/or other pulp mill or a paper mill waste by-products having different solids content. For example, a liquor could be used to dilute a sludge to a desired solids content. If the solids content of a pulp or paper mill waste by-product is too low it can be concentrated by evaporation, centrifugation, and or combining with another composition having a relatively higher solids content. For example, a sludge could be added to a liquor to increase the solids content. In some embodiments, a target solids content for a pulp or paper mill waste by-product (liquor and/or sludge) can be in the range from 10 to 80%, from 20 to 70%, or even from 25 to 40%.

In some embodiments, a pulp or paper mill waste by-product can be sterilized if desired before hydrolysis and/or propagation. For example, a pulp or paper mill waste by-product can be sterilized by exposing the pulp mill or a paper mill waste by-product to a temperature in the range from 215° F. to 270° F. for a time period in the range from 30 seconds to 5 minutes. The pulp mill or a paper mill waste by-product can be agitated (e.g., mixed) during sterilizations so that the pulp mill or a paper mill waste by-product can be uniformly exposed to the desired temperature throughout.

In some embodiments, the pH of a pulp or paper mill waste by-product can be adjusted if desired before hydrolysis and/or propagation. The pH of a pulp or paper mill waste by-product can be adjusted to a pH in the range from 4 to 7, or even 5-6. A variety of substances such as acid or base can be used to adjust the pH of a pulp or paper mill waste by-product. For example, a red liquor tends to be acidic so a basic substance can be added to increase its pH. As another example, black liquor tends to be alkaline so an acidic substance can be added to reduce its pH.

In some embodiments, a pulp or paper mill waste by-product includes one or more monosaccharides as a waste by-product. In other embodiments, a pulp or paper mill waste by-product (e.g., a liquor and/or a sludge) includes one or more polysaccharides that need to be broken down into monosaccharides before it can be used for propagation by a microorganism. In some embodiments, one or more polysaccharides in a pulp or paper mill waste by-product can be hydrolyzed to form a saccharified composition having one or more monosaccharides prior to being combined with a cell mass of microorganisms for propagation. Alternatively, if desired, one or more polysaccharides in a pulp or paper mill waste by-product can be hydrolyzed during propagation. For example, a pulp or paper mill waste by-product can be combined with a first cell mass of microorganisms, and one or more enzymes so that one or more polysaccharides in the pulp or paper mill waste by-product can be simultaneously hydrolyzed while the microorganisms propagate and consume the one or more monosaccharides that are generated from hydrolysis.

A non-limiting example of hydrolyzing one or more polysaccharides in a pulp or paper mill waste by-product to form a saccharified composition is described herein below.

In some embodiments, depending on the undissolved solids content of a pulp or paper mill waste by-product, the pulp or paper mill waste by-product may be liquefied before saccharification. Liquefaction can be performed for a variety of reasons. For example, if the undissolved solids content is too high, a pulp or paper mill waste by-product can be relatively difficult to transport (e.g., pump) and/or to difficult to agitate (e.g., mix). Liquefying a pulp or paper mill waste by-product can reduce its viscosity and make it easier to process. Liquefaction can also make a pulp or paper mill waste by-product more accessible to enzymes and/or chemicals used in saccharifcation.

Liquefaction involves breaking down at least polysaccharides so as to reduce the viscosity of the liquefaction composition so that a relatively higher solids content can be further processed (e.g., saccharified). In some embodiments, at least a pulp or paper mill waste by-product; an ionic stabilizing component; and one or more enzymes can be combined to form a liquefaction composition and hydrolyze at least a portion of one or more polysaccharides in the pulp or paper mill waste by-product. Water (e.g., water that has been treated via reverse osmosis) can be added to the liquefaction composition as well. Water can be obtained from a variety of sources such as tap water, process water (e.g., from a biorefinery), and/or from a pulp or paper mill waste by-product liquor as described herein. The liquefaction composition can be exposed to conditions for hydrolyzing at least a portion of one or more polysaccharides in the pulp or paper mill waste by-product and form a liquefied composition.

In some embodiments, while not being bound by theory it is believed that pulp or paper mill waste by-products may lack one or more components that can facilitate enzymatic activity during enzymatic hydrolysis of one or more polysaccharides present in the pulp or paper mill waste by-product. For example, one or more components (e.g., minerals, dirt, ash) that may typically be present with raw materials, especially on an industrial scale, may be absent (e.g., due to washing) to an undue degree in a pulp or paper waste by-product. If present, such minerals or other components may provide desirable ionic stabilizing properties for enzymes in a liquefaction composition to facilitate desirable enzymatic activity during enzymatic hydrolysis of one or more polysaccharides present in the pulp or paper mill waste by-products.

According to the present disclosure, one or more ionic stabilizing ingredients can be combined with the pulp or paper mill waste by-product, and one or more enzymes to provide a source of ions having a desirable ionic strength at least in the liquefaction medium and/or saccharification medium to facilitate enzymatic activity during enzymatic hydrolysis (e.g., during liquefaction and/or saccharification). In some embodiments, an ionic stabilizing component can include one or more salts (e.g., sea salt and/or a buffering salt (e.g., potassium phosphate)), a stillage composition, corn steep liquor, a pulp or paper mill waste by-product liquor, and combinations thereof.

In some embodiments, the ionic stabilizing ingredient can include a stillage composition. A stillage composition can include whole stillage, thin stillage, condensed thin stillage (e.g., syrup), wet cake, and combinations thereof. Whole stillage is a byproduct of distilling a fermentation product that includes one or more biochemicals. For example, a process for making whole stillage is a corn grain-to-ethanol process. In some embodiments, a stillage composition is derived from a grain ethanol process (e.g., milled grain ethanol process). In some embodiments, milled grain includes wet-milled grain and/or dry-milled grain. Non-limiting examples of grain include corn, soybean, sorghum, wheat, rice, barley, oats, millet, rye or any other grains that that are capable of being fermented. Either the ground whole grain can be used or only one or more portions of the grain can be used. For example, whole grains can be dry milled for fermentation or fractionated into one or more separated portions before milling. After milling, the milled grain material can be further processed to break down polysaccharides and/or oligosaccharides into one or more monosaccharides such as glucose that can be fermented by, e.g., yeast. Methods of breaking down polysaccharides such as starch into glucose include e.g. hot water, such as hot water that includes an added acid such as sulfuric acid. Methods of breaking down starch into glucose also include enzymatic hydrolysis, which can avoid relatively higher temperatures used, e.g., in jet-cooking and, thereby, avoid undue degradation of other grain components that may be beneficial for hydrolysis of a sludge as described herein and/or for propagation as described herein. An example of such enzymatic hydrolysis is described in U.S. Pat. No. 7,842,484 (Lewis) and is referred to as saccharification of raw grain starch "without cooking." After fermentation, the fermentation product is distilled in a system where the ethanol is removed from the fermented mash in a distillation column. After the ethanol is removed, the remaining residue is removed as stillage residue. The stillage residue is known as "whole stillage." The whole stillage can be optionally further processed via one or more systems to further clarify or separate the whole stillage before being delivered to a propagation system. For example, the whole stillage can be subjected to a solid-liquid separation process to produce a solid stream, also known as wet cake, and a liquid stream, also referred to as thin stillage. The thin stillage can be further processed to increase the solids concentration by evaporation resulting in condensed thin stillage (syrup). Examples of creating a stillage composition are described in U.S. Pat. No. 7,842,484 (Lewis), U.S. Pat. No. 7,919,291 (Lewis et al.), and U.S. Pub. No. 2005/0239181 (Lewis et al.), wherein the entireties of said patent documents are incorporated herein by reference.

In some embodiments, a stillage composition can be combined with the other components in a range of amounts. The amount on volumetic basis can depend on what type of stillage composition is used. For example, in some embodiments, a thin stillage composition having a solids content in the range from 4-10 percent on a dry basis can be included in amount from 1 percent to 50 percent by volume of the total liquefaction composition (e.g., from 5 percent to 25 percent by volume of the total liquefaction composition, or even from 5 percent to 15 percent by volume of the total liquefaction composition). The amount on a percent of total solids basis can be applied among multiple types of stillage compositions. For example, in some embodiments, a thin stillage or concentrated thin stillage (syrup) may be included in an amount in the range from 0.5 to 0.8 percent solids on a dry basis of the total liquefaction composition.

In some embodiments, the ionic stabilizing component includes a buffering salt. While buffering salts can be used to adjust pH, they can also be used to provide a source of ions for desirable enzyme activity as described herein. A buffering salt can be combined with the other components (e.g., liquor and/or sludge, enzyme, and water) as a solution having a buffering salt concentration in the range from 0.1 M to 10 M. In some embodiments, the volumetric ratio of a buffering salt solution to a stillage composition can be in the range of from 0.05 to 25, or even 1 to 10.

In some embodiments, one or more ionic stabilizing ingredients can be present in an amount to provide a desirable ionic strength as measured by a conductivity value. Conductivity of a composition such as a liquefaction composition can be readily measured and reported in units of Sieverts/cm. In some embodiments, one or more ionic stabilizing ingredients can be present in an amount in a liquefaction composition so that the liquefaction composition has a conductivity in the range from 1 microSiemen/cm to 50 milliSiemens/cm, from 40 microSiemens/cm to 40 milliSiemens/cm or even from 5 milliSiemens/cm to 30 milliSiemens/cm.

One or more enzymes that can hydrolyze polysaccharides present in the pulp or paper mill waste by-product include cellulase enzymes and hemicellulose enzymes. In some embodiments, the one or more enzymes can be present in an amount from 0.005 to 0.5 grams of enzyme per dry gram of pulp or paper mill waste by-product, or even from 0.01 to 0.1 grams of enzyme per dry gram of pulp or paper mill waste by-product. Enzymatic hydrolysis of pulp is disclosed in U.S. Pub. No.: 2011/0250638 (Sjoede et al.), wherein the entirety of said patent document is incorporated herein by reference.

After combining the pulp or paper mill waste by-product with one or more enzymes and an ionic stabilizing component to form a liquefaction composition, the liquefaction composition can be maintained at a temperature in the range from 45 to 75° C., or even from 55 to 65° C., and a pH in the range from 4 to 7, or even 5-6, for a time period in the range from 5-15 hours, or even from 6-10 hours, to form a liquefied composition. In some embodiments, the liquefaction process can be a continuous liquefaction process by continuously feeding pulp or paper mill waste by-product, enzymes, water, and ionic stabilizing ingredients into a continuous stirred tank reactor (CSTR) and continuously removing liquefied composition. The feed and discharges rates from the reactor can be selected to provide the appropriate residence time in the reactor. A CSTR can facilitate vigorous mixing of the reactor contents to facilitate dispersing the enzymes and providing a uniform medium that is conducive to enzymatic activity. Alternatively, a fed-batch system could be used for liquefaction.

After liquefaction, the liquefied composition can be exposed to conditions to form a saccharified composition that includes monosaccharides. In some embodiments, the monosaccharides include xylose and/or glucose. For example, the liquefied composition can be transferred into a batch saccharification reactor and maintained at a temperature in the range from 45 to 75° C., or even from 55 to 65° C., and a pH in the range from 4 to 7, or even 5-6, for a time period in the range from 30 to 60 hours, or even from 35 to 55 hours, to form the saccharified composition.

In some embodiments, the saccharified composition has a total solids content (dissolved and undissolved solids) in the range from 15 to 50 percent, from 15 to 35, or even from 20 to 30 percent. Advantageously, such solids content can produce sufficient amounts of one or more monosaccharides to generate very desirable populations of microorganisms for subsequent fermentation.

In some embodiments, the saccharified composition is not treated after it is formed such as by filtering and the like. After saccharification, a first cell mass of microorganisms can be added to a propagation medium that includes the saccharified composition in a manner so that the microorganisms can propagate.

The source of one or more monosaccharides derived from a pulp or paper mill waste by-product can be present in a propagation medium in a wide variety of amounts. The amount can depend on a variety of factors. For example, the amount can depend on the desired amount of monosaccharides and can, therefore, depend on whether a pulp and/or paper mill waste by-product sludge is used, whether a pulp and/or paper mill waste by-product liquor is used, or whether a combination of such a sludge and a liquor is used. The amount can also depend on whether the pulp or paper mill waste by-product is hydrolyzed prior to propagation or during propagation. The amount can also depend on whether a stillage composition is included to facilitate enzymatic hydrolysis as explained above. In some embodiments, a pulp or paper mill waste by-product liquor or sludge can be present in amount from 1 to 99 percent by volume of the total propagation medium, from 30 to 99 percent by volume of the total propagation medium, from 50 to 99 percent by volume of the total propagation medium, or even from 80 to 99 percent by volume of the total propagation medium. In some embodiments, a pulp or paper mill waste by-product sludge can be present in an amount in the range from 1 to 5 percent by weight of the total propagation medium.

In some embodiments, the source of one or more monosaccharides derived from a pulp or paper mill waste by-product (e.g., the saccharified composition) is the sole carbon source and nutrient source in the propagation medium.

Optionally, one or more additional components can be included in the propagation medium. For example, additional water can be added as desired to adjust the solids content. As another example, one or more additional components can be included in the propagation medium to function as a carbon sources and/or nutrient source. In some embodiments, the propagation medium can include a stillage composition (e.g. whole stillage, thin stillage, wet cake, condensed thin stillage (e.g., syrup), and mixtures thereof). Stillage compositions are discussed above with respect to enzymatic hydrolysis. A stillage composition added to a propagation medium can be the same as, or different from, any stillage composition that is used in enzymatic hydrolysis of a pulp or paper mill waste by-product as discussed above. While not being bound by theory, it is believed that a stillage composition can be used as a pH buffer to help maintain a pH that facilitates propagation. The stillage composition may also be a source of ions that can facilitate propagation. As one example, the stillage composition may function as an ionic stabilizing ingredient (as discussed above) if hydrolysis of a pulp or paper mill waste by-product is performed simultaneously with propagation.

The stillage composition can be added to a propagation medium in any amount so as to help reproduce (propagate) and generate a desired population of microorganism within a given amount of time. The amount of stillage composition provided can depend on factors such as the type and amount of other carbon and/or other nutrient sources present, pH of a pulp or paper mill waste by-product, temperature during propagation, desired time period for propagation, total solids of the propagation medium, and the like. In some embodiments, the propagation medium includes only a pulp or paper mill waste by-product as described herein, and a stillage composition (thin stillage) as the carbon and nutrient sources. In some embodiments, the stillage composition can be present in an amount in the range from 1 to 50 grams of dry solids per liter of propagation medium, from 5 to 40 grams of dry solids per liter of propagation medium, or even from 10 to 30 grams of dry solids per liter of propagation medium. The weight ratio of the stillage composition to the pulp or paper mill waste by-product can be selected to facilitate propagation. The weight ratio can depend on, e.g., the solids content of the stillage composition and the pulp or paper mill waste by-product and/or the type of stillage composition and the pulp mill or paper mill waste by-product. In some embodiments, the weight ratio of the stillage composition to the pulp or paper mill waste by-product (liquor or sludge) can from 0.01 to 40, from, or even from 1 to 30 on a dry weight basis.

Another example of additional components that can be included in the propagation medium include urea, ammonium, vitamins, diammonium phosphate, potash, yeast extract, combinations of these, and the like.

A first cell mass of microorganisms can be combined with the source of one or more monosaccharides derived from a pulp or paper mill waste by-product (and any other components that are part of the propagation medium such as a stillage composition) to form a propagation composition. The propagation composition can then be exposed to propagation conditions to propagate the first cell mass of the microorganism into a second cell mass of the microorganism. A propagation composition can include at least a propagation medium and a first cell mass of the microorganism. In some embodiments, the propagation medium makes up the vast majority of the propagation composition. In some embodiments, a propagation medium is present in amount from 0.1 to 100 percent by volume of the propagation composition, 1 to 99 percent by volume of the propagation composition, or even 5 to 95 percent by volume of the propagation composition.

In some embodiments, the propagation composition is aerated and/or agitated (stirred) for at least a portion of the propagation process so as to help provide sufficient oxygen levels throughout the composition so as to promote aerobic respiration and, therefore, reproduction of the microorganism instead of, e.g., anaerobic fermentation. In some embodiments, the propagation composition is aerated for the entire duration of propagation. Exemplary aeration rates include from 0.5 to 1 volumetric units of air per volumetric units of propagation composition per minute (vvm). Propagating microorganisms is also disclosed in U.S. Pat. No. 9,340,767 (Narendranath); U.S. Pat. No. 9,034,631 (Narendranath et al.); U.S. Pat. No. 8,450,094 (Narendranath et al.); U.S. Pat. No. 9,234,167 (Narendranath et al.); U.S. Pat. No. 9,416,376 (Narendranath et al.); U.S. Pub. No. 2015/0368679 (Narendranath et al.); U.S. Pub. No. 2018/0171285 (Narendranath et al.); WO Pub. No. 2017/091361 (Karl); and WO Pub. No. 2017/218380 (Sarks et al.), wherein the entireties of said patent documents are incorporated herein by reference.

A propagation composition can be held at a temperature in the range from 20° C. to 40° C. (e.g., about 31-32° C.) for a time period of from 10-40 hours (e.g., about 20-30 hours) to propagate the first cell mass of the microorganism into a second cell mass of the microorganism. The pH of the propagation composition can be from 5-7, or even from 5-6. If needed, the pH can be controlled by adding a wide variety of pH controlling substances that are compatible with microorganism to be propagated.

In some embodiments, the second cell mass of the microorganism is at least 200 times greater in number than the first cell mass of the microorganism, at least 1000 times greater in number than the first cell mass of the microorganism, at least 1500 times greater in number than the first cell mass of the microorganism, at least 2000 times greater in number than the first cell mass of the microorganism, or even at least 3000 times greater in number than the first cell mass of the microorganism.

In some embodiments, the second cell mass of the microorganism is $1 \times 10^7$ cells per milliliter of propagation composition or more, $5 \times 10^7$ cells per milliliter of propagation composition or more, $1 \times 10^8$ cells per milliliter of propagation composition or more, $5 \times 10^8$ cells per milliliter of propagation composition or more, or even $1 \times 10^9$ cells per milliliter of propagation composition or more.

Optionally, one or more additional components can be added to form a propagation composition. For example, make-up water can be added if more water is desired.

After a desirable population of microorganisms is formed (propagated), then at least a portion of the second cell mass of microorganisms can be added to another source of one or more monosaccharides so that the at least a portion of the second cell mass of organism can convert the one or more monosaccharides (e.g., xylose and/or glucose) into a biochemical (e.g., ethanol). For example, at least a portion of the second cell mass of microorganisms can be added to another source of one or more monosaccharides derived from a pulp or paper mill waste by-product (as described herein above). It is noted that the sources of one or more monosaccharides derived from a pulp or paper mill waste by-product used in propagation and fermentation can both be derived via hydrolysis of one or more of pulp sludge, pulp liquor, paper sludge, paper liquor, and mixtures thereof and, therefore, may be compositionally the same or different.

Because methods and systems according to the present disclosure can process relatively high solids levels of a pulp or paper mill waste by-product during liquefaction and/or saccharification, this leads to desirable ethanol titers during fermentation, especially in a commercial scale biorefinery where liquefaction can operate at a high solids level as described herein on a continuous basis. In some embodiments, fermentation of a saccharified composition (broth) produced according to the present disclosure can produce a beer having at least 5 percent by volume of ethanol, at least 7 percent by volume of ethanol, or even at least 10 percent by volume of ethanol.

Example 1

Figure 1:
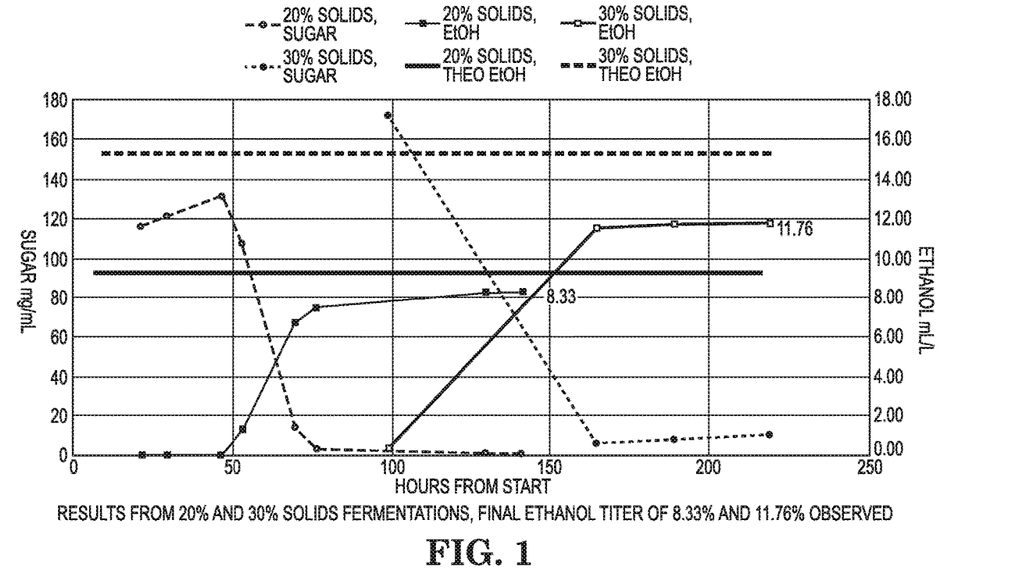
FIG. 1 is a graph showing results for Example 1.

This example measured fermentable sugars and ethanol titer for saccharified compositions prepared according to the present disclosure and having a 20% final total solids and a final volume of 1 liter of slurry, and 30% final total solids and a final volume of 1 liter of slurry. As can be seen in FIG. 1, a graph shows total fermentable sugars versus time and ethanol titer from that reaction versus time. The straight lines show the total theoretical ethanol titer.

For each trial, 178.33 mL of reverse osmosis water, 100 mL of thin stillage (5% total solids) and 50 mL of 5.5 pH potassium phosphate buffer were mixed in a reactor. 16.5 mL of an enzyme was added, which corresponds to a loading rate of enzyme of 0.066 gram enzyme/gram dry sludge solids. The enzyme was capable of facilitating hydrolysis of hemicellulose and cellulose. The pH was maintained from 5.0-5.5. The pH was adjusted with 10% ammonia or 10% sulfuric acid as necessary. Pulp sludge was added "as is," meaning that the sludge solids were not dried. For this size reactor the final target was 666.67 grams of as is sludge solids. Initially, 100 grams of sludge solids were added and mixed at 55 Cat 150 RPM for 1 hour. Next, 50 grams of sludge solids were added at a time until all of the remaining 566.67 grams were added. After the final solids were added, the contents of the reactor were mixed while kept at 55 C for an additional amount of time. The pH was maintained in the range of 5.0-5.5 throughout liquefaction and saccharification. The 20% total solids trial was hydrolyzed for 47 hours while the 30% total solids trial was hydrolyzed for 99 hours. The data for sugar concentration during hydrolysis was taken after the mixtures became liquid so the data points do not begin at zero. At the end of saccharification, the temperature was lowered to 32 C while the pH was maintained at 5.5. Next 1 gram of active yeast/liter was added to the reactor with 4 mL of Lactoside 247™ for bacterial control. Fermentation was allowed to progress for 94 hours (until 141 hour point in FIG. 1) for the 20% total solids trial and for 120 hours (until the 219 hour point in FIG. 1) for the 30% total solids trial.

Example 2

This example shows red liquor fermentation results when using yeast propagated on yeast extract, peptone, glucose, and xylose compared to yeast propagated on yeast extract, peptone, glucose, and red liquor. The yeast were propagated aerobically in 500 mL baffled Erlenmeyer flasks with Air-O-Top seals. The propagation media contained 1% yeast extract, 2% peptone, and 2% glucose in reverse osmosis (RO) water for both propagations, while one propagation additionally contained 1% xylose (hereby referred to as YEP) and the other additionally contained red liquor to 1% total sugar (hereby referred to as YEPL). The yeast were propagated at 30° C. from a concentration of about 0.01-0.02 g/L dry yeast concentration to 5 g/L dry yeast concentration (~20 h for YEP and ~24 h for YEPL). While not being bound by theory, the YEPL propagation may have taken longer because of osmotic stress on the yeast due to one or more inhibitors (e.g., salts such as magnesium sulfate) in the red liquor. The optical density (OD) was measured at 600 nm using a spectrophotometer to determine the dry yeast concentration using an OD vs dry yeast concentration calibration. Based on the dry yeast concentrations, a specific mass of yeast was obtained from each propagation using centrifugation and then re-suspended in thin stillage to create a crème at 40 g/L dry yeast concentration. The thin stillage was derived from a starch saccharification process "without cooking", an example of which is described in U.S. Pat. No. 7,842,484 (Lewis). The yeast suspension from each propagation was then added to fermentation flasks at 0.5 g/L or 5 g/L. At inoculation, the fermentation flasks contained, on a percent total volume basis, 90% red liquor (pH adjusted to 5.5 using 30% ammonium hydroxide), 10% thin stillage (pH adjusted to 5.5 using 30% ammonium hydroxide), 2 ppm Lactoside 247™ for bacterial control, and the previously mentioned yeast crème. The fermentations were performed using an ANKOM RF Gas Production System and shaking air incubator at 32° C. for 72 h. The ANKOM system measures fermentation performance by cumulatively measuring the amount of carbon dioxide produced; any carbon dioxide produced is assumed to have been produced from the fermentation of sugar into ethanol.

Figure 2:
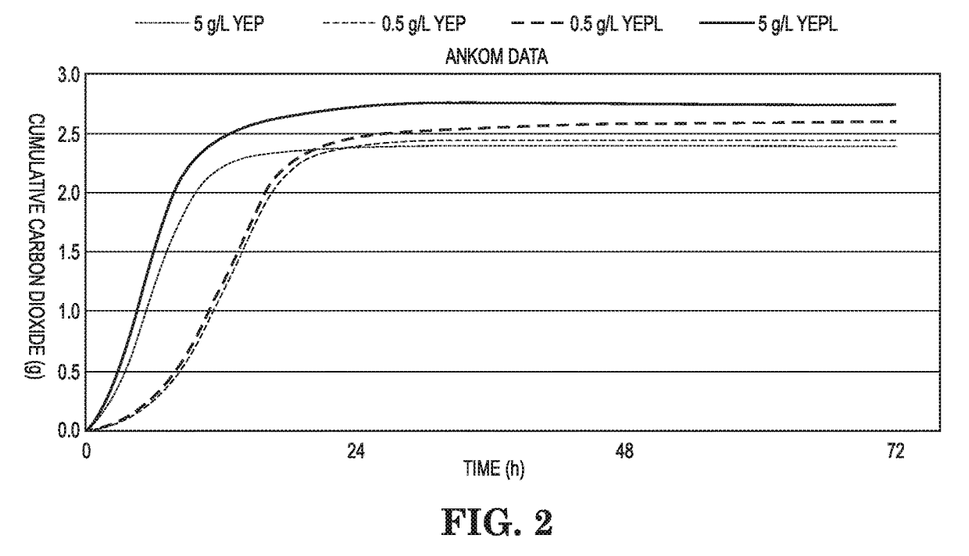
FIG. 2 is a graph showing results for Example 2.
Figure 3:
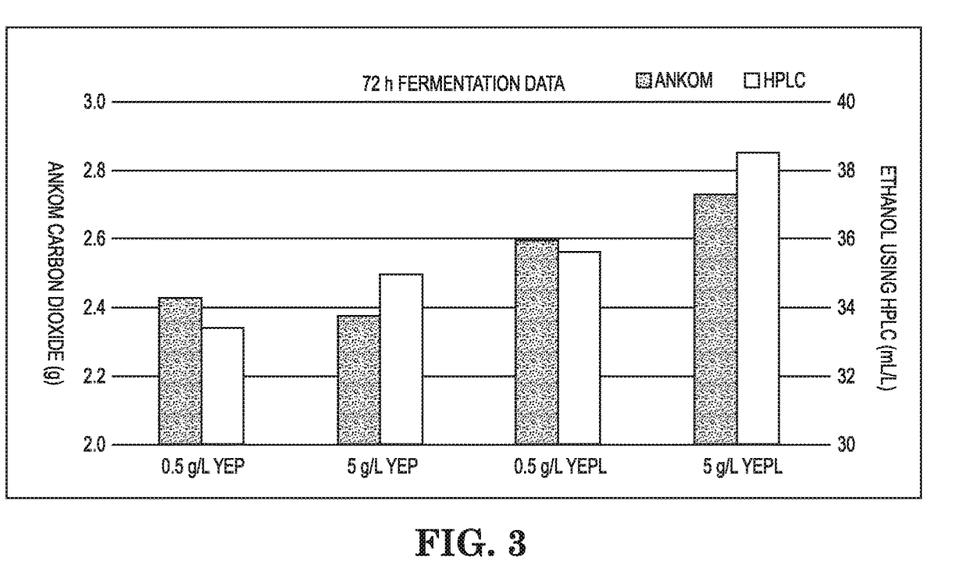
FIG. 3 is a graph showing results for Example 2.

The results in FIG. 2 shows that higher cumulative carbon dioxide were and faster fermentation kinetics were obtained when using propagations containing red liquor (YEPL) compared to propagations not containing red liquor (YEP). FIG. 3 also includes HPLC measurements for ethanol production and shows that higher ethanol titers were obtained when using propagations containing red liquor (YEPL) compared to propagations not containing red liquor (YEP).

The red liquor included the following monosaccharides in the approximate amounts shown in parenthesis: glucose (1.5% w/v), xylose (0.9% w/v), galactose (0.7% w/v), and mannose (4.5% w·v). High performance liquid chromatography (HPLC) showed that galactose was consumed the fastest out of the monosaccharides present in red liquor.

Additional embodiments according to the present disclosure are described below.

Embodiment 1

A method of processing a pulp or paper mill waste by-product, wherein the method comprises:
   a) forming a liquefaction composition, wherein the liquefaction composition comprises:
      i) a pulp or paper mill waste by-product;
      ii) an ionic stabilizing component; and
      iii) one or more enzymes that can hydrolyze at least a portion of one or more polysaccharides in the pulp mill or a paper mill waste by-product;

b) exposing the liquefaction composition to conditions to hydrolyze at least a portion of one or more polysaccharides in the pulp mill or a paper mill waste by-product and form a liquefied composition.

Embodiment 2

The method of embodiment 1, wherein the ionic stabilizing component comprises a stillage composition derived from a grain ethanol process (e.g., dry-grind or wet-milled grain ethanol process).

Embodiment 3

The method of embodiment 2, wherein the stillage composition is chosen from whole stillage, thin stillage, condensed thin stillage (e.g., syrup), wet cake, and combinations thereof.

Embodiment 4

The method of embodiment 2, wherein the stillage composition is added to the liquefaction composition in an amount from 1 percent to 50 percent by volume of the total liquefaction composition (e.g., from 5 percent to 25 percent by volume of the total liquefaction composition, or even from 5 percent to 15 percent by volume of the total liquefaction composition).

Embodiment 5

The method of embodiment 1, wherein the ionic stabilizing component is chosen from one or more salts (e.g., sea salt and/or a buffering salt (e.g., potassium phosphate)), a stillage composition, corn steep liquor, a pulp or paper mill waste by-product liquor, and combinations thereof.

Embodiment 6

The method of embodiment 5, wherein the ionic stabilizing component comprises a buffering salt and a stillage composition, wherein the buffering salt is added to the liquefaction composition as a solution having a buffering salt concentration in the range from 0.1 M to 10 M, and wherein the volumetric ratio of the solution to the stillage composition is in the range of from 0.05 to 25.

Embodiment 7

The method of embodiment 6, wherein the one or more enzymes are present in an amount from 0.005 to 0.1 grams of enzyme per dry gram of pulp sludge and/or paper sludge.

Embodiment 8

The method of embodiment 1, wherein the liquefaction composition is maintained at a temperature in the range from 45 to 75° C. and a pH in the range from 4 to 7 for a time period in the range from 5-15 hours to form the liquefied composition.

Embodiment 9

The method of embodiment 1, wherein the liquefaction composition has a total solids (dissolved and undissolved solids) in the range from 15 to 45 percent, from 15 to 35, or even from 15 to 30 percent.

Embodiment 10

The method of embodiment 1, further comprising exposing to liquefied composition to conditions to form a saccharified composition comprising monosaccharides, wherein the monosaccharides comprise xylose and/or glucose.

Embodiment 11

The method of embodiment 10, wherein the liquefied composition is transferred into a batch saccharification reactor and maintained at a temperature in the range from 45 to 60° C. and a pH in the range from 4 to 7 for a time period in the range from 30 to 60 hours to form the saccharified composition.

Embodiment 12

The method of embodiment 11, further comprising adding a cells mass of microorganisms (e.g., bacteria or yeast) to the saccharified composition in a manner so that the microorganisms can convert at least the xylose and/or glucose into a biochemical (e.g., ethanol).

Embodiment 13

A system for processing pulp mill or a paper mill waste by-product, wherein the system comprises:
  a) at least one liquefaction tank reactor containing a liquefaction composition, wherein the liquefaction composition comprises:
    i) a pulp or paper mill waste by-product;
    ii) an ionic stabilizing component; and
    iii) one or more enzymes that can hydrolyze at least a portion of one or more polysaccharides in the pulp mill or a paper mill waste by-product, wherein the at least one liquefaction tank reactor is configured (adapted) to expose the liquefaction composition to conditions to hydrolyze at least a portion of one or more polysaccharides in the pulp mill or a paper mill waste by-product and form a liquefied composition.

What is claimed is:
1. A method of propagating a microorganism, the method comprising:
  a) combining at least one pulp or paper mill waste by-product and an ionic stabilizing component, wherein the at least one pulp or paper mill waste by-product is chosen from a pulp sludge, a paper sludge, and combinations thereof, wherein the ionic stabilizing component is chosen from one or more salts, at least one stillage composition, corn steep liquor, at least one pulp or paper mill waste by-product liquor, and combinations thereof, and wherein the at least one stillage composition is derived from a grain starch ethanol process,
  b) enzymatically hydrolyzing one or more polysaccharides and/or one or more oligosaccharides present in at least one pulp or paper mill waste by-product in the presence of one or more enzymes and into one or more monosaccharides, wherein the one or more enzymes are chosen from one or more cellulase enzymes, one or more hemicellulose enzymes, and combinations thereof;
  c) providing a first cell mass of a microorganism that can convert one or more monosaccharides into a biochemical via fermentation; and d) propagating the first cell mass of the microorganism in a propagation composition that comprises one or more monosaccharides from the enzymatic hydrolysis as a carbon source to propagate the first cell mass of the microorganism into a second cell mass of the microorganism.

2. The method of claim 1, wherein the enzymatic hydrolysis and the propagating occur simultaneously.

3. The method of claim 2, wherein the propagation composition has a conductivity from 1 microSiemen/cm to 50 milliSiemens/cm.

4. The method of claim 2, wherein the propagation composition has a conductivity from 40 microSiemens/cm to 40 milliSiemens/cm.

5. The method of claim 1, wherein the enzymatic hydrolysis occurs before the propagating.

6. The method of claim 1, wherein the ionic stabilizing component comprises at least one liquor derived from a sulphite pulping process.

7. The method of claim 6, wherein the ionic stabilizing component further comprises at least one stillage composition chosen from thin stillage, condensed thin stillage, and combinations thereof.

8. The method of claim 1, wherein the ionic stabilizing component comprises at least one stillage composition chosen from whole stillage, thin stillage, condensed thin stillage, wet cake, and combinations thereof.

9. The method of claim 8, wherein a weight ratio of the at least one stillage composition to the at least one pulp or paper mill waste by-product is from 0.01 to 40 on a dry weight basis.

10. The method of claim 8, wherein a weight ratio of the at least one stillage composition to the at least one pulp or paper mill waste by-product is from 1 to 30 on a dry weight basis.

11. The method of claim 1, wherein the second cell mass of the microorganism is at least 200 times greater in number than the first cell mass of the microorganism.

12. The method of claim 1, wherein the first cell mass of the microorganism is $5 \times 10^6$ cells per milliliter of the propagation composition or less, and the second cell mass of the microorganism is $1 \times 10^8$ cells per milliliter of the propagation composition or more.

13. The method of claim 1, wherein the microorganism comprises an ethanologen.

14. The method of claim 13, wherein the ethanologen comprises non-genetically modified *Saccharomyces cerevisiae* and/or *Saccharomyces cerevisiae* that has been genetically modified to convert xylose and glucose into ethanol.

15. The method of claim 1, further comprising fermenting at least a portion of the second cell mass in the presence of one or more monosaccharides to convert the one or more monosaccharides into a biochemical.

16. The method of claim 1, wherein the grain starch ethanol process comprises enzymatically hydrolyzing the grain starch with one or more amylase enzymes.

17. The method of claim 1, wherein the pulp sludge and/or the paper sludge has been washed prior to the enzymatic hydrolysis.

18. The method of claim 1, wherein the ionic stabilizing component comprises corn steep liquor.

19. A method of propagating a microorganism, the method comprising:
a) combining at least one pulp or paper mill waste by-product and an ionic stabilizing component, wherein the at least one pulp or paper mill waste by-product is chosen from a pulp sludge, a paper sludge, and combinations thereof, and wherein the ionic stabilizing component is chosen from one or more salts, corn steep liquor, at least one pulp or paper mill waste by-product liquor, and combinations thereof,
b) enzymatically hydrolyzing one or more polysaccharides and/or one or more oligosaccharides present in at least one pulp or paper mill waste by-product in the presence of one or more enzymes and into one or more monosaccharides, wherein the one or more enzymes are chosen from one or more cellulase enzymes, one or more hemicellulose enzymes, and combinations thereof;
c) providing a first cell mass of a microorganism that can convert one or more monosaccharides into a biochemical via fermentation; and
d) propagating the first cell mass of the microorganism in a propagation composition that comprises one or more monosaccharides from the enzymatic hydrolysis as a carbon source to propagate the first cell mass of the microorganism into a second cell mass of the microorganism.

20. The method of claim 19, wherein the pulp sludge and/or the paper sludge has been washed prior to the enzymatic hydrolysis.

* * * * *